United States Patent
Birdsley et al.

(10) Patent No.: US 6,864,972 B1
(45) Date of Patent: Mar. 8, 2005

(54) IC DIE ANALYSIS VIA BACK SIDE LENS

(75) Inventors: Jeffrey D. Birdsley, Cedar Park, TX (US); Michael R. Bruce, Austin, TX (US); Brennan V. Davis, Austin, TX (US); Rosalinda M Ring, Leominster, MA (US); Daniel L. Stone, Cedar Park, TX (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 106 days.

(21) Appl. No.: 10/205,766

(22) Filed: Jul. 26, 2002

Related U.S. Application Data
(60) Provisional application No. 60/307,996, filed on Jul. 26, 2001.

(51) Int. Cl.[7] ............................................... G01N 21/88
(52) U.S. Cl. ................. 356/237.4; 356/237.5; 438/18; 438/29
(58) Field of Search ................ 356/237.1, 237.2–237.5, 356/239.1–239.3, 600, 601; 250/559.4–559.49; 438/14–18, 29; 65/37, 61, 65–66, 102–110; 264/1.37

(56) References Cited

U.S. PATENT DOCUMENTS

| | | | | |
|---|---|---|---|---|
| 5,220,403 A | * | 6/1993 | Batchelder et al. | .......... 356/450 |
| 5,247,392 A | * | 9/1993 | Plies | ........................... 359/661 |
| 5,604,635 A | * | 2/1997 | Lawandy | .................... 359/620 |

* cited by examiner

Primary Examiner—Richard A. Rosenberger
Assistant Examiner—Vincent P. Barth

(57) ABSTRACT

The present invention is directed analysis of a flip-chip integrated circuit die having SOI structure that improves the ability to image and analyze selected portions of circuitry in the die. According to an example embodiment of the present invention, a lens is formed in a back side of a flip-chip die and over the insulator portion of SOI structure in the die. Light is directed at the lens and the lens is used to focus the light to target circuitry in the die. A reflection from the circuitry is detected and used to analyze the die, such as by imaging the circuitry in the die and identifying defects therein. The lens formed in the die enhances the ability to focus light to selected circuitry in the die and improves the ability to analyze dies having SOI structure through the insulator.

20 Claims, 3 Drawing Sheets

IC DIE ANALYSIS VIA BACK SIDE LENS

This is a conversion of U.S. Provisional Patent Application Ser. No. 60/307,996, filed on Jul. 26, 2001, to which Applicant claims priority under 35 U.S.C. § 119(e).

FIELD OF THE INVENTION

The present invention relates generally to semiconductor devices and their fabrication and, more particularly, to semiconductor devices and their manufacture involving the analysis and debugging of circuitry within an integrated circuit.

BACKGROUND OF THE INVENTION

The semiconductor industry has recently experienced technological advances that have permitted dramatic increases in circuit density and complexity, and equally dramatic decreases in power consumption and package sizes. Present semiconductor technology now permits single-chip microprocessors with many millions of transistors, operating at speeds of hundreds of millions of instructions per second to be packaged in relatively small, air-cooled semiconductor device packages. A by-product of such high-density and high functionality in semiconductor devices has been the demand for increased numbers of external electrical connections to be present on the exterior of the die and on the exterior of the semiconductor packages which receive the die, for connecting the packaged device to external systems, such as a printed circuit board.

As the manufacturing processes for semiconductor devices and integrated circuits increase in difficulty, methods for testing and debugging these devices become increasingly important. Not only is it important to ensure that individual chips are functional, it is also important to ensure that batches of chips perform consistently. In addition, the ability to detect a defective manufacturing process or manufacturing design early is helpful for reducing the number of defective devices manufactured and improving the design process.

To increase the number of pad sites available for a die, different chip packaging techniques have been used. One technique is referred to as a dual in-line package (DIP) in which bonding pads are along the periphery of the device. Another technique, called controlled-collapse chip connection or flip chip packaging, uses the bonding pads and metal (solder) bumps. The bonding pads need not be on the periphery of the die and hence are moved to the site nearest the transistors and other circuit devices formed in the die. As a result, the electrical path to the pad is shorter. Electrical connections to the package are made when the die is flipped over the package with corresponding bonding pads. Each bump connects to a corresponding package inner lead. The resulting packages have a lower profile and have lower electrical resistance and a shortened electrical path. The output terminals of the package may be ball-shaped conductive-bump contacts (usually solder or other similar conductive material) and are typically disposed in a rectangular array. These packages are occasionally referred to as "Ball Grid Array" (BGA). Alternatively, the output terminals of the package may be pins, and such a package is commonly known as the pin grid array (PGA) package.

For BGA, PGA and other types of packages, once the die is attached to the package, the backside portion of the die remains exposed. The transistors and other circuitry are generally formed in a very thin epitaxially grown silicon layer on a single crystal silicon wafer of which the die is singulated from. In one example structural variation, a layer of insulating material, such as silicon dioxide, is formed on one surface of a single crystal silicon wafer followed by the thin epitaxially grown silicon layer containing the transistors and other circuitry. This wafer structure is termed "silicon on insulator" (SOI) and, when silicon dioxide is used, the insulating layer is called the "buried oxide layer" (BOX).

In some instances the orientation of the die with the circuit side face down on a substrate may be a disadvantage or present new challenges. For example, when a circuit fails or when it is necessary to modify a particular chip, access to the transistors and circuitry near the circuit side is typically obtained only from the backside of the chip. This is challenging for IC dies including those having SOI structure because the transistors are in a very thin layer (about 10 micrometers) of silicon covered by the buried oxide layer (less than about 1 micrometer) and the bulk silicon (greater than 500 micrometers). Thus, access for viewing the circuit side of the flip chip die is challenging using conventional techniques, such as optical or scanning electron microscopy.

SUMMARY OF THE INVENTION

The present invention is directed to the analysis of a flip-chip IC die having SOI structure. The present invention is exemplified in a number of implementations and applications, some of which are summarized below.

According to an example embodiment of the present invention, an integrated circuit die having SOI structure is analyzed using a lens formed in the die. The lens is formed in a back side of the die, over an insulator portion of the SOI structure and adapted for viewing selected circuitry in a circuit side of the die. A light source is directed at the selected circuitry via the lens, and an image of the selected circuitry is obtained. The lens can be used to view circuitry through the insulator portion of the SOI structure, allowing the circuitry to be imaged without necessarily damaging or otherwise altering the insulator portion of the SOI structure. The back side lens is particularly useful for addressing challenges to the analysis of integrated circuit dies, including those mentioned in the Background, and improves the ability to obtain an image of circuitry that would be affected by the removal of the insulator portion of the SOI structure.

In another example embodiment of the present invention, a system is adapted for analyzing an integrated circuit die having SOI structure. The system includes a formation arrangement adapted to form a lens in a back side of the die and over the insulator portion of the SOI structure. A tight source is adapted to direct light at selected circuitry in the die via the lens, and an image of the selected circuitry is detected at a detection arrangement adapted to detect light reflecting from the circuitry and through the lens. In a more particular implementation, the light source and the detection arrangement are part of a single device.

The above summary of the present invention is not intended to describe each illustrated embodiment or every implementation of the present invention. The figures and detailed description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
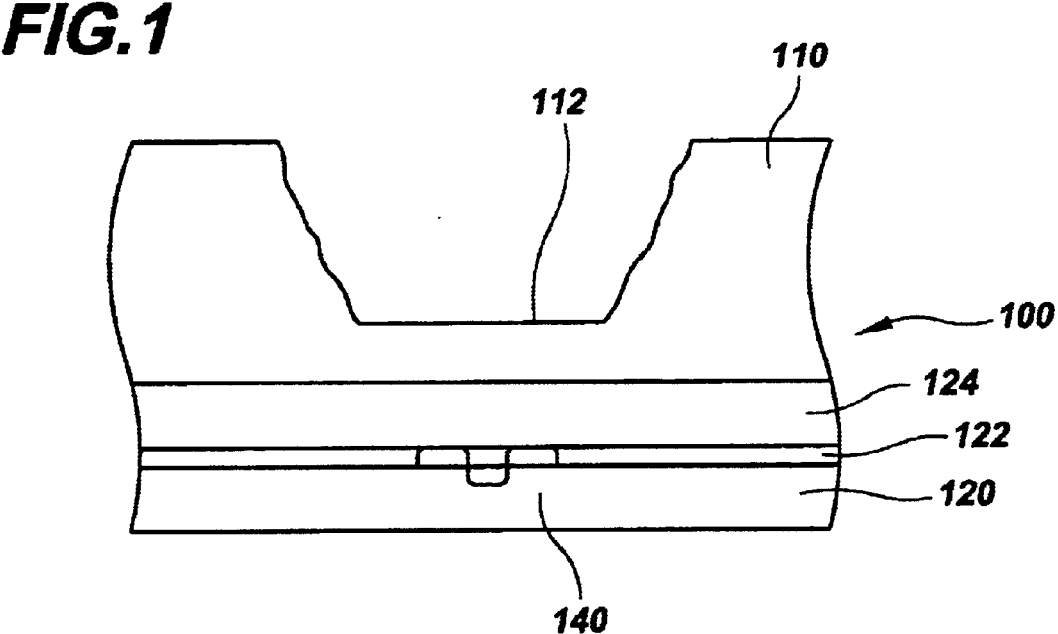
FIG. 1 is a flip-chip integrated circuit die undergoing analysis, according to an example embodiment of the present invention.

While the invention is amenable to various modifications and alternative forms, specifics thereof have been shown by way of example in the drawings and will be described in detail. It should be understood, however, that the intention is not necessarily to limit the invention to the particular embodiments described. On the contrary, the intention is to cover all modifications, equivalents, and alternatives falling within the spirit and scope of the invention as defined by the appended claims.

DETAILED DESCRIPTION

The present invention is believed to be applicable for a variety of different types of semiconductor devices, and the invention has been found to be particularly suited for flip-chip integrated circuit dies having silicon on insulator (SOI) structure. While the present invention is not necessarily limited to such SOI devices, various aspects of the invention may be appreciated through a discussion of various examples using this context.

According to an example embodiment of the present invention, an integrated circuit die having circuitry including SOI structure in a circuit side opposite a back side is analyzed. A lens is formed in the back side of the die, over an insulator portion of the SOI structure and adapted for viewing selected circuitry in the die. The placement and formation of the lens is selected for viewing the selected circuitry. In one implementation, a portion of substrate in the back side is removed and the lens is formed in a void formed by the substrate removal. In another implementation, the back side is globally thinned and the lens is formed on the thinned surface. Once the lens is formed, a light source is directed through the lens and the lens is used to focus the light on the selected circuitry. Reflected light from the circuitry passes back through the lens and is used to obtain an image of the selected circuitry.

The lens is formed in various manners, depending upon the die to be analyzed, the available equipment, and the type of lens to be formed. For example, in one particular implementation, an optical nanomachining (or micromachining) system is used to form a lens in a selected region of the integrated circuit die without necessarily affecting surrounding circuitry. The nanomachining system (or micromachining system) includes a femtosecond laser beam adapted to remove substrate at a target area of a selected region in the die, and is used to create an opening in which the lens is formed. An example femtosecond laser that can be used in connection with the present invention includes a CPA-2001 available from Clark-MXR, Inc.

The portion of the die at which the lens is placed is selected in response to the characteristics of the die, the lens and the analysis to be performed. A sufficient depth and placement of the lens is achieved when a desired response can be obtained via the lens for the selected application. In one implementation, the die is thinned so that a thickness of about 100 microns over the insulator portion remains. The lens is formed in the thinned portion of the die and used to analyze the circuitry. In another instance, the back side is thinned to expose the insulator portion of the SOI structure, and the lens is formed thereon. In still another implementation, a portion of the insulator is removed and the lens is placed therein.

In another implementation, a polishing arrangement is adapted to form the lens from material formed in the back side of the die. The polishing arrangement includes one or more of a chemical-mechanical polishing (CMP) device, a laser polishing device, a focused ion beam (FIB) device and an etching device. The lens is polished to form a selected shape that facilitates the viewing of target circuitry in the die.

In another example embodiment of the present invention, a solid immersion lens (SIL) is built in the die. The solid immersion lens is shaped like a truncated sphere and focuses incident light to a single spot at the base of the truncated sphere. Effectively, the SIL slows down light passing through it to a fraction of its normal speed in air, which shortens the light's wavelength and creates a very fine spot to which the light is focused. The index of refraction of the material used for the SIL determines the spot size of the light being focused, based in part upon the following equation:

$$d = \frac{\lambda}{2*NA*n};$$

wherein
  d=Diameter of spot of light;
  λ=Wavelength of light;
  NA =Numerical aperture of objective lens; and
  n =Refractive index of SIL.

The NA is that of the objective lens being used to view the circuitry, such as the lens of a microscope or other viewing device. The SIL raises the effective numerical aperture of the objective. Materials used for the SIL with a high index of refraction produce higher effective NA than those with a lower index of refraction. This focused light is then used to illuminate and obtain an image from selected circuitry in the die. The SIL is particularly useful for obtaining an image of circuitry formed in close proximity to other circuitry because the lens allows the light to be focused to a spot that is smaller than can be obtained using conventional devices.

Various materials may be used to form the lens. For example, in one implementation, diamond is used. Diamond is useful because it has an index of refraction of about 2.4, and thus can be used to focus the light to a spot having a diameter of less than half of the diameter of the incident light focused by the objective lens used (e.g., the refractive index is inversely proportional to the diameter of the spot of light, as shown in the equation hereinabove). Diamond is first deposited in the back side of the die using conventional techniques, such as sputtering, chemical vapor deposition (CVD), or other suitable process. Once the diamond is deposited it is machined and/or polished to form the lens. Other materials, such as glass (index of refraction of about 1.5) or aluminum oxide maybe used in place of diamond to address cost, availability and other needs.

In another example embodiment of the present invention, a plurality of lenses is formed in the integrated circuit die during the manufacture of the die. The lenses are formed at selected areas to observe circuitry of interest in the die at a later time. This is particularly useful for monitoring selected circuitry known to exhibit defects or have a history of exhibiting defects, such as circuitry located in a critical circuit path. When the die is to be analyzed, light is directed via one or more of the plurality of lenses to selected circuitry in the die.

FIGS. 1–3A show an integrated circuit die 100 undergoing analysis, according to an example embodiment of the present invention. The integrated circuit die has a circuit side 120 opposite a back side 110, and circuitry 140 formed as part of SOI structure including silicon 122 formed over an insulator 124. A portion of substrate in the back side 110 is removed and an exposed portion 112 is formed therein. The depth and location of the exposed portion is selected to facilitate the viewing of the circuitry 140.

Figure 2:
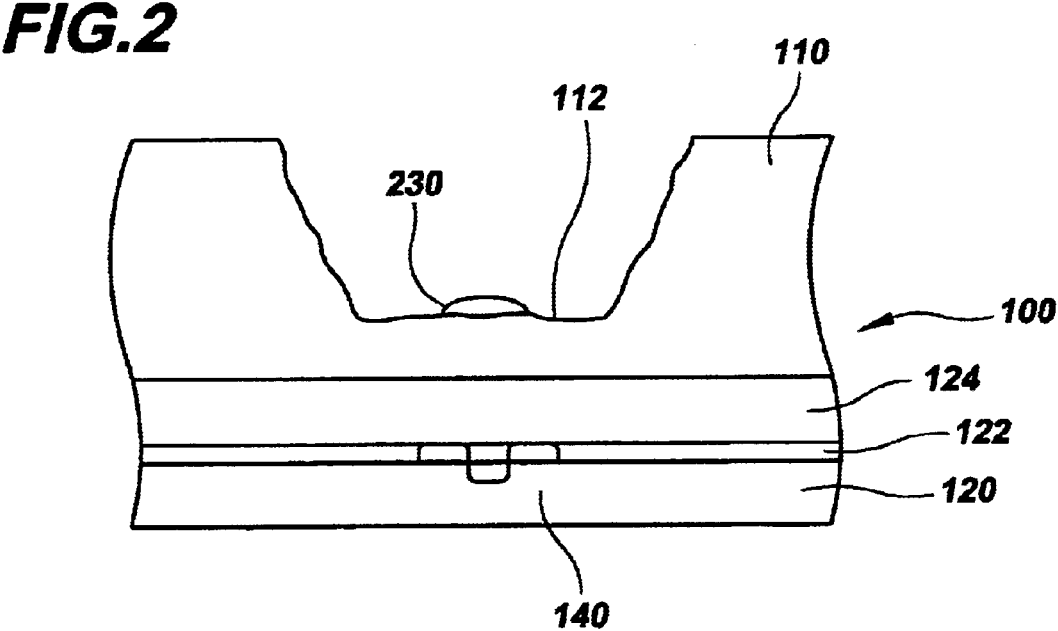
FIG. 2 is a flip-chip integrated circuit die undergoing analysis, according to another example embodiment of the present invention.
Figure 3A:
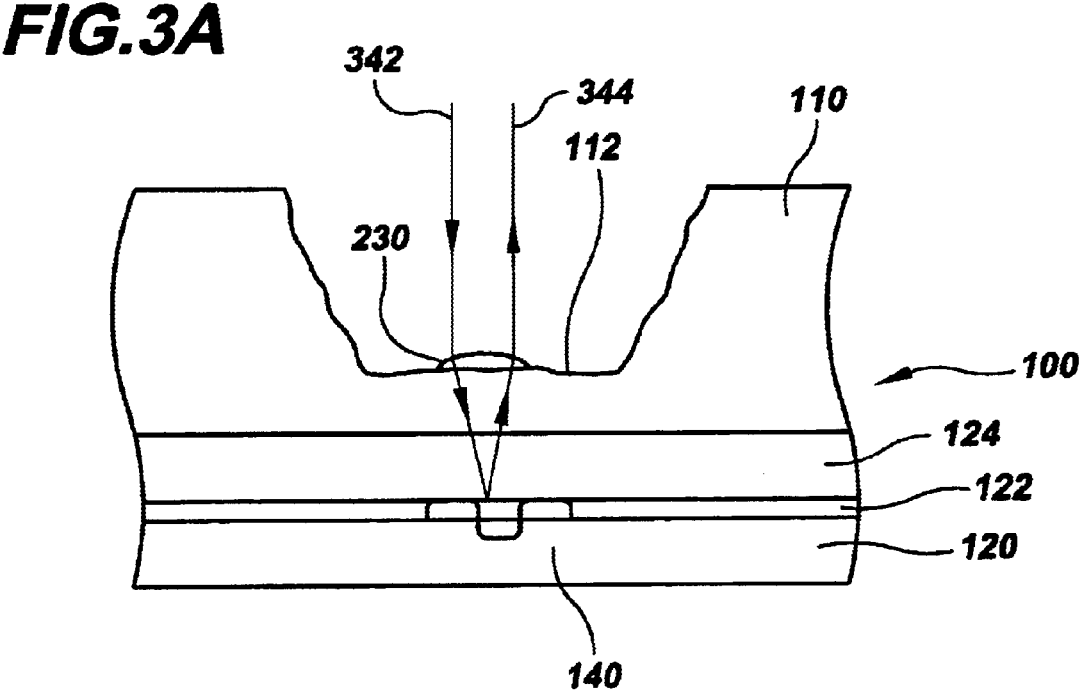
FIG. 3A is a flip-chip integrated circuit die undergoing analysis, according to another example embodiment of the present invention.

In FIG. 2, a lens 230 is formed at the exposed portion 112 in the back side of the die using one or more techniques, such as those described hereinabove. The lens is located over the insulator portion 124 of the SOI structure, as well as over the circuitry 140. In FIG. 3A, light 342, such as laser light, is directed at the selected circuitry 140 via the lens 230. The lens is used to focus the light to the circuitry, and reflected light 344 passes through the lens and is used to obtain an image of the die.

Figure 3B:
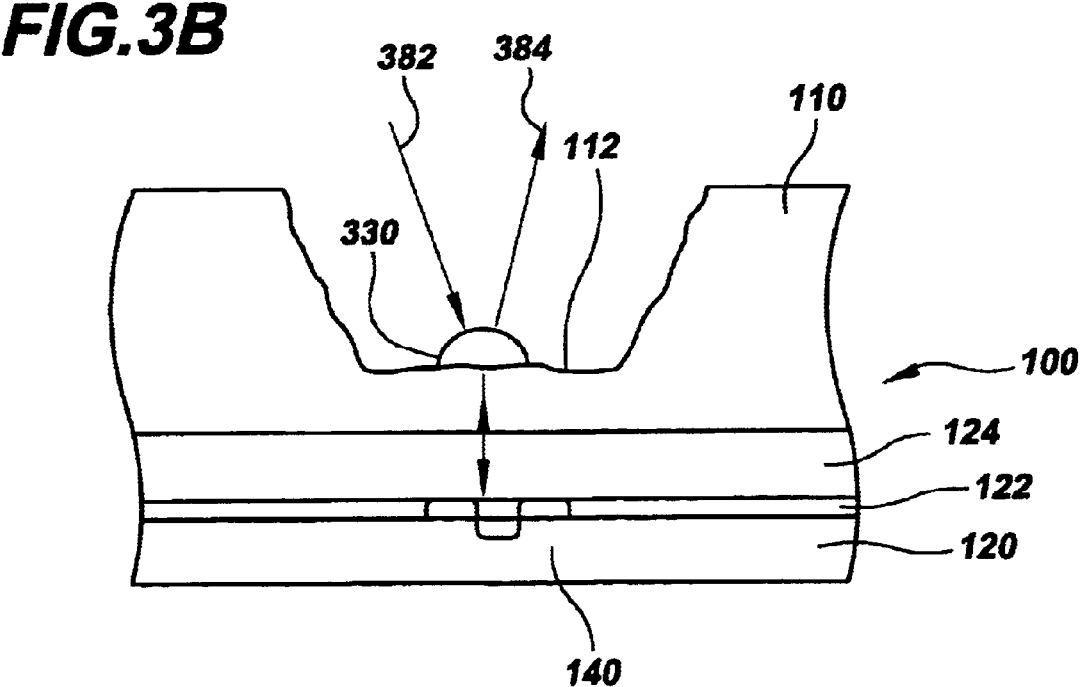
FIG. 3B is a flip-chip integrated circuit die undergoing analysis, according to another example embodiment of the present invention.

In another example embodiment of the present invention, FIG. 3B shows a SIL 330 formed in the back side 110 of the integrated circuit die 100. In this example embodiment, light 382 directed at the lens is focused to a smaller spot and transmitted from the lens to the circuitry 140. The light is reflected as reflected light 384 and used to obtain an image of the circuitry.

Figure 3C:
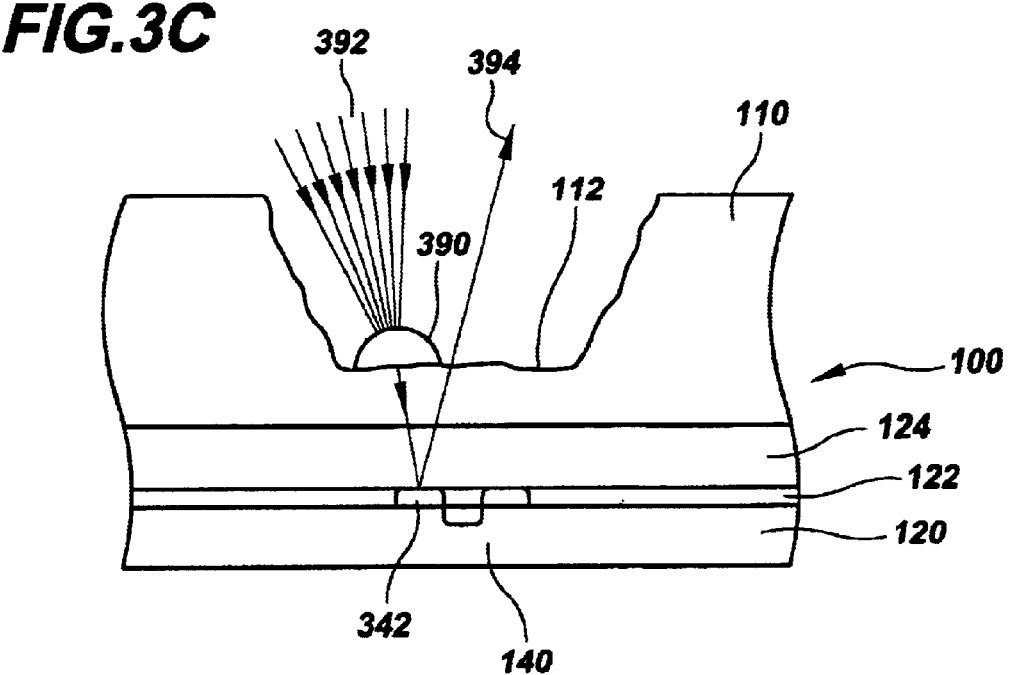
FIG. 3C is a flip-chip integrated circuit die undergoing analysis, according to another example embodiment of the present invention.

As discussed herein, the placement of the lens is selected to meet the needs of the particular application in which the lens is to be used. FIG. 3C shows a SIL 390 formed at an angle and adapted to focus a beam 392 of incident light to a source/drain region 342 of a selected portion of circuitry 140. The SIL is used to focus the light to a smaller spot than the beam of light would have made, and makes possible the illumination of a very small portion of circuitry. In one implementation, light having a wavelength of about 685 nanometers is used, and the lens is adapted to focus the light to a spot of less than about 0.25 microns. A reflection 394 of the focused light from the source/drain region 342 passes from the die and is detected and used to obtain an image of the source/drain region 342.

Figure 4:
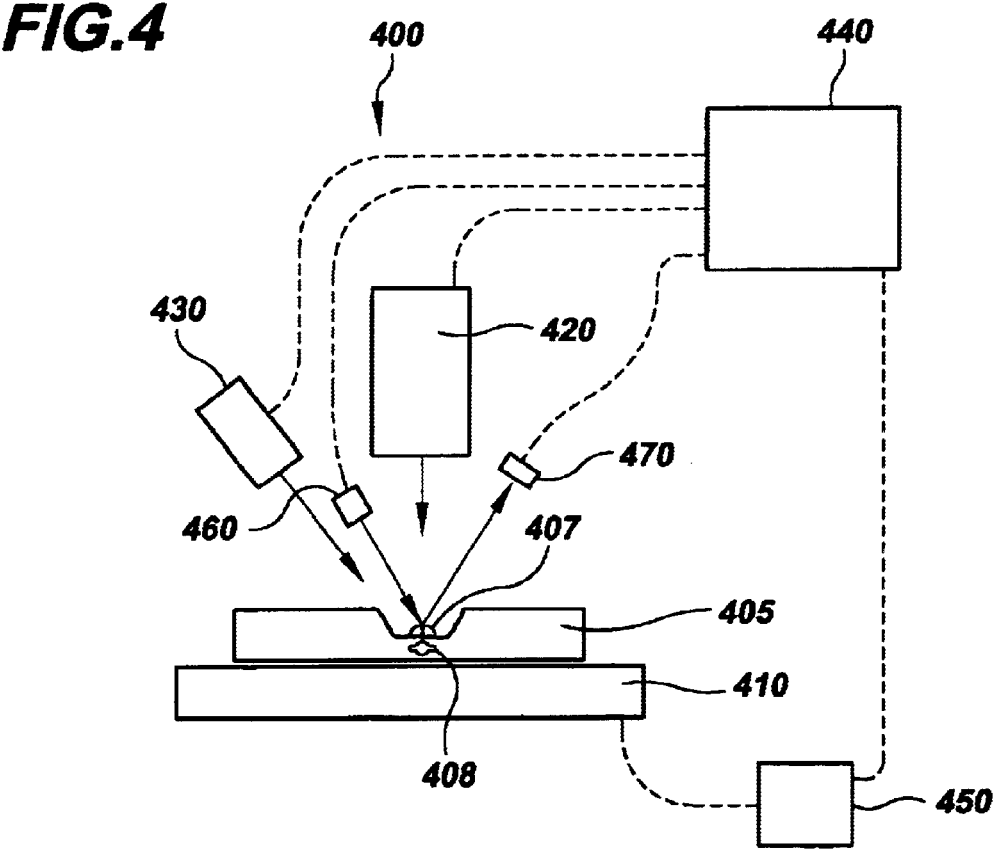
FIG. 4 is a system for analyzing a flip-chip integrated circuit die, according to another example embodiment of the present invention.

FIG. 4 is a system 400 for analyzing a semiconductor die, according to another example embodiment of the present invention. The system includes a stage 410 adapted to hold a die 405 to be analyzed. A substrate removal device 430 is adapted to remove substrate from a portion of the die 405 and form an exposed region in a back side of the die into which a lens can be formed. A formation device 420 is adapted to deposit lens material, such as diamond, into the exposed region. The deposited material is used to make a lens 407 in the die.

The formation arrangement may include one or more of the following: a CVD arrangement, a laser deposition arrangement, a nano-machining arrangement and a polishing arrangement. In one implementation (not shown), the system 400 includes a nanomachining arrangement adapted to machine material deposited by the formation device 420 into the lens 407.

A light source 460 is adapted to direct light having a selected wavelength at a portion of target circuitry 408 in the die via the lens 407. The lens focuses the light and a detector 470, such as a photodiode, microscope, a camera, a near IR camera or other light detector, is adapted to detect a reflection of the light from the target circuitry. The detected reflection is used to obtain an image of the die including the target circuitry. In one implementation, the light source and the detector are included in a laser scanning microscope (LSM) adapted to direct laser light at the target circuitry and obtain an image thereof.

In an alternate example embodiment of the present invention, a stimulation device 450 is electrically coupled to the stage 410 and to the die 405 via electrical connections between the stage in the die. The stimulation device is used to power the die, provide signals to the die, and/or to otherwise stimulate the die. The stimulated die is then imaged using the components described hereinabove.

In a further example embodiment of the present invention, a computer 440 is optionally communicatively coupled to one or more of the following: the formation device 420, the substrate removal device 430, the light source 460, the light detector 470 and the stimulation device 450. The computer is programmed to communicate with and/or control the components to which it is connected. In the instance that the computer is communicatively coupled to the light detector 470, it is further adapted to provide an image of the die.

While the present invention has been described with reference to several particular example embodiments, those skilled in the art will recognize that many changes may be made thereto without departing from the spirit and scope of the present invention, which is set forth in the following claims.

What is claimed is:

1. A method for analyzing a flip chip integrated circuit die having silicon on insulator (SOI) structure and circuitry in a circuit side opposite a back side, the insulator portion being between the circuitry and the back side, the method comprising;

forming a lens over the insulator of the SOI structure and in the back side of the die;

directing light at a selected portion of circuitry in the die via the lens; and using a portion of the directed light that is reflected from the die and obtaining an image of the selected portion of circuitry therefrom.

2. The method of claim 1, wherein forming the lens includes forming the lens during at least one of: the manufacture of the die and post-manufacturing analysis of the die.

3. The method of claim 1, wherein forming the lens includes using a nano-machining laser.

4. The method of claim 3, wherein forming the lens includes forming the lens over a circuit portion suspected of having a defect.

5. The method of claim 1, wherein forming the lens includes polishing a portion of material in the die.

6. The method of claim 1, further comprising removing substrate from the back side and forming an exposed region prior to forming the lens, and wherein forming a lens includes forming a lens in the pack side at the exposed region.

7. The method of claim 1, wherein forming a lens includes forming a solid immersion lens.

8. The method of claim 1, wherein forming a lens includes depositing a material including at least one of diamond, glass, and aluminum oxide.

9. The method of claim 1, wherein directing light includes directing a laser at the die.

10. The method of claim 1, wherein directing light includes using the lens to focus the light at the selected portion of circuitry.

11. The method of claim 1, wherein directing light and obtaining an image include using a laser scanning microscope (LSM).

12. A system for analyzing a flip chip integrated circuit die having silicon on insulator (SOI) structure and circuitry in a circuit side opposite a back side, the insulator portion being between the circuitry and the back side, the system comprising;

means for forming a lens over the insulator and in the back side;

means for directing light at a selected portion of circuitry in the die via the lens; and means for using a portion of the directed light that is reflected from the die and obtaining an image of the selected portion of circuitry therefrom.

13. A system for analyzing a flip chip integrated circuit die having silicon on insulator (SOI) structure and circuitry in a circuit side opposite a back side, the insulator portion being between the circuitry and the back side, the system comprising;

a formation arrangement adapted to form a lens over the insulator and in the back side;

a light source adapted to direct light at a selected portion of circuitry in the die via the lens; and a detection device adapted to detect a portion of the directed light that is reflected from the die and obtain an image of the selected portion of circuitry therefrom.

14. The system of claim 13, further including a microscope adapted and arranged to view images projected through the lens.

15. The system of claim 13, wherein the light source includes a laser light source.

16. The system of claim 15, wherein the laser light source includes a nano-second laser.

17. The method of claim 13, further comprising a substrate removal device adapted to remove substrate from the back side and form an exposed region into which a lens can be formed.

18. The system of claim 13, wherein the detection arrangement includes at least one of: a microscope, a camera, a near IR camera and a laser-scanning microscope.

19. The system of claim 14, wherein the formation arrangement includes at least one of: a CVD arrangement, a laser deposition arrangement, a nano-machining arrangement and a polishing arrangement.

20. The system of claim 14, wherein the formation arrangement is further adapted to form a built in solid immersion lens.

* * * * *